United States Patent [19]
Cohen et al.

[11] Patent Number: 5,792,042
[45] Date of Patent: Aug. 11, 1998

[54] APPARATUS FOR TREATING INCONTINENCE IN FEMALES

[76] Inventors: Kenneth L. Cohen, 9 Bishop Dr., Woodbridge, Conn. 06525; Dennis J. Hanlon, 15 Morris Rd., East Haven, Conn. 06513

[21] Appl. No.: 694,330

[22] Filed: Aug. 8, 1996

[51] Int. Cl.⁶ ....................................................... A61F 2/00
[52] U.S. Cl. ...................... 600/29; 600/30; 600/31; 128/DIG. 25
[58] Field of Search ................ 600/29–32; 128/DIG. 25, 128/834–836

[56] References Cited

U.S. PATENT DOCUMENTS

| | | |
|---|---|---|
| 2,616,429 | 11/1952 | Merenlender . |
| 3,331,371 | 7/1967 | Rocchi et al. . |
| 3,459,175 | 8/1969 | Miller . |
| 3,503,400 | 3/1970 | Osthagen . |
| 3,646,929 | 3/1972 | Bonnar . |
| 3,797,478 | 3/1974 | Walsh et al. . |
| 3,811,448 | 5/1974 | Morton . |
| 3,811,450 | 5/1974 | Lord . |
| 3,812,841 | 5/1974 | Isaacson . |
| 3,841,304 | 10/1974 | Jones . |
| 3,854,469 | 12/1974 | Giori et al. . |
| 3,866,611 | 2/1975 | Baumrucker . |
| 3,903,894 | 9/1975 | Rosen et al. . |
| 3,939,821 | 2/1976 | Roth . |
| 4,022,216 | 5/1977 | Stevens . |
| 4,209,009 | 6/1980 | Henning . |
| 4,256,093 | 3/1981 | Helms et al. . |
| 4,350,161 | 9/1982 | Davis . |
| 4,428,365 | 1/1984 | Hakky . |
| 4,432,757 | 2/1984 | Davis, Jr. . |
| 4,457,299 | 7/1984 | Cornwell . |
| 4,553,533 | 11/1985 | Leighton . |
| 4,579,554 | 4/1986 | Glassman . |
| 4,587,954 | 5/1986 | Haber . |
| 4,610,664 | 9/1986 | Harle . |
| 4,610,665 | 9/1986 | Matsumoto et al. . |
| 4,619,245 | 10/1986 | Haber et al. . |
| 4,634,443 | 1/1987 | Haber . |
| 4,673,393 | 6/1987 | Suzuki et al. . |
| 4,682,592 | 7/1987 | Thorsgard . |
| 4,692,152 | 9/1987 | Emde . |
| 4,813,935 | 3/1989 | Haber et al. . |
| 4,846,784 | 7/1989 | Haber . |
| 4,909,785 | 3/1990 | Burton et al. . |
| 4,932,958 | 6/1990 | Reddy et al. . |
| 5,030,199 | 7/1991 | Barwick et al. . |
| 5,090,424 | 2/1992 | Simon et al. ............... 600/29 |
| 5,112,306 | 5/1992 | Burton et al. . |
| 5,181,921 | 1/1993 | Makita et al. . |
| 5,234,409 | 8/1993 | Goldberg ............... 604/96 |
| 5,344,397 | 9/1994 | Heaven et al. . |
| 5,352,182 | 10/1994 | Kalb et al. . |
| 5,417,226 | 5/1995 | Juma . |
| 5,476,434 | 12/1995 | Kalb et al. . |

*Primary Examiner*—Jennifer Bahr
*Assistant Examiner*—Rosiland Kearney
*Attorney, Agent, or Firm*—Bachman & Lapointe, P.C.

[57] ABSTRACT

An apparatus for treating incontinence in females includes an elongate body member having a first end and a second end; an internal plug member positioned at the first end of the body member; an external retaining member positioned at the second end, at least one member of the internal plug member and the external retaining member being moveable longitudinally with respect to the other member of the internal plug member and the retaining member; and a member for longitudinally securing the at least one member relative to the other member, whereby the elongate body member can be positioned in a urethra with the plug member positioned at an interior opening of the urethra and with the retaining member positioned at an exterior opening of the urethra.

39 Claims, 2 Drawing Sheets

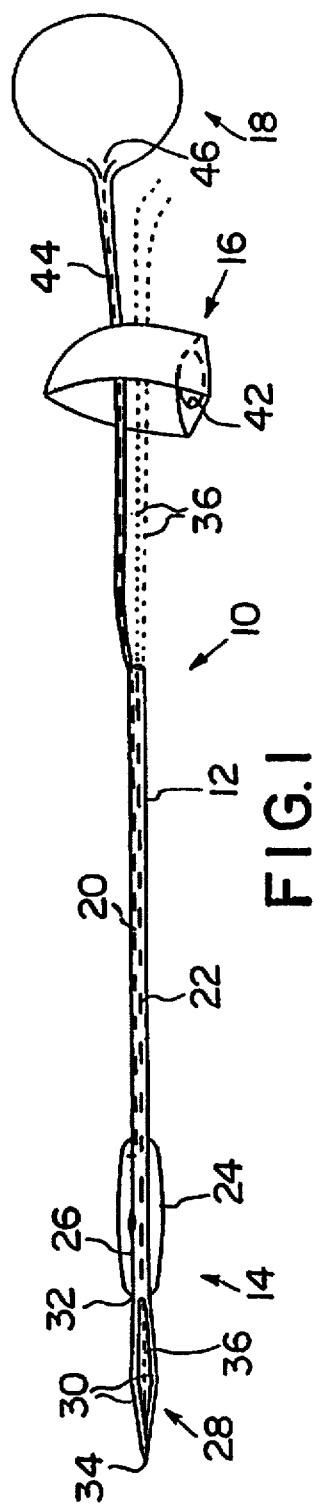
FIG.1
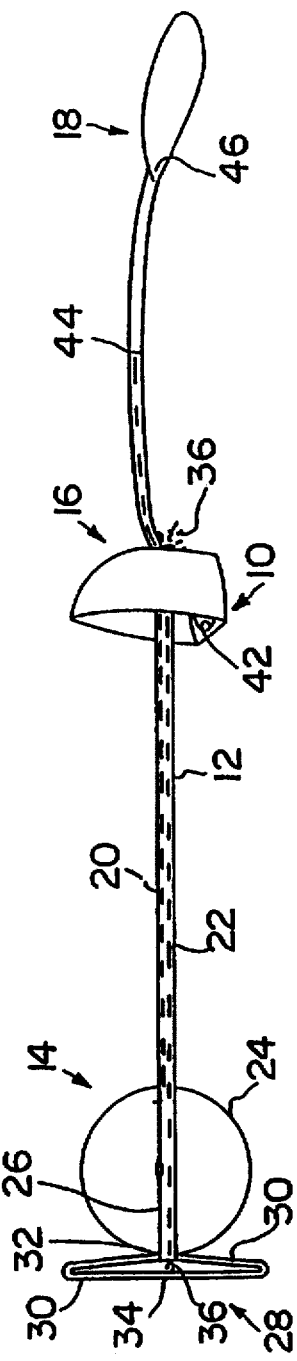
FIG.2
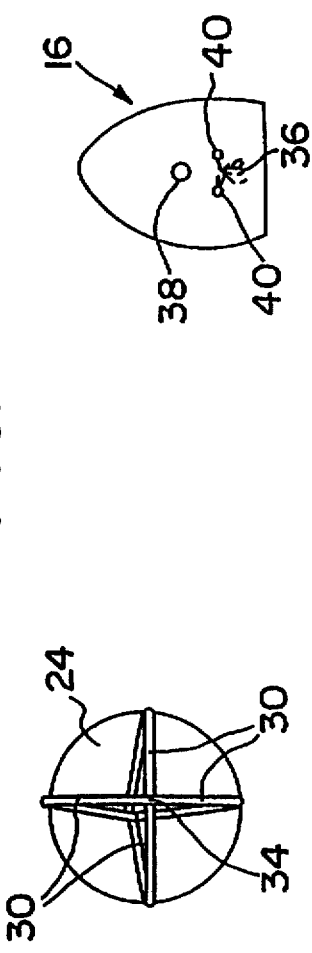
FIG.3
FIG.4

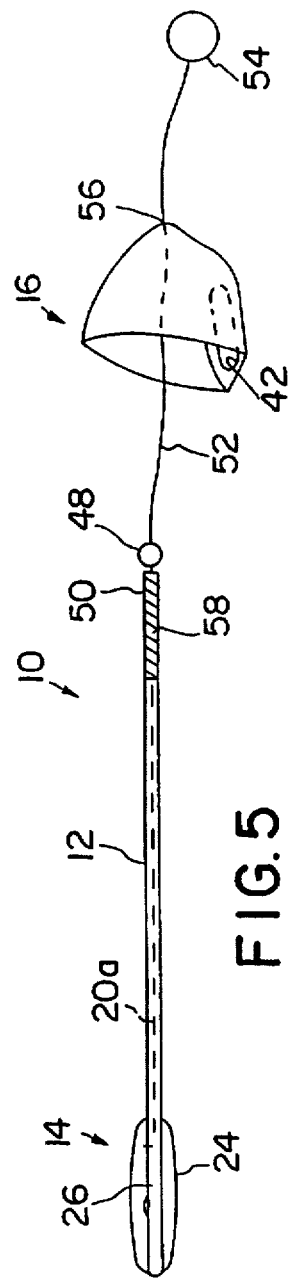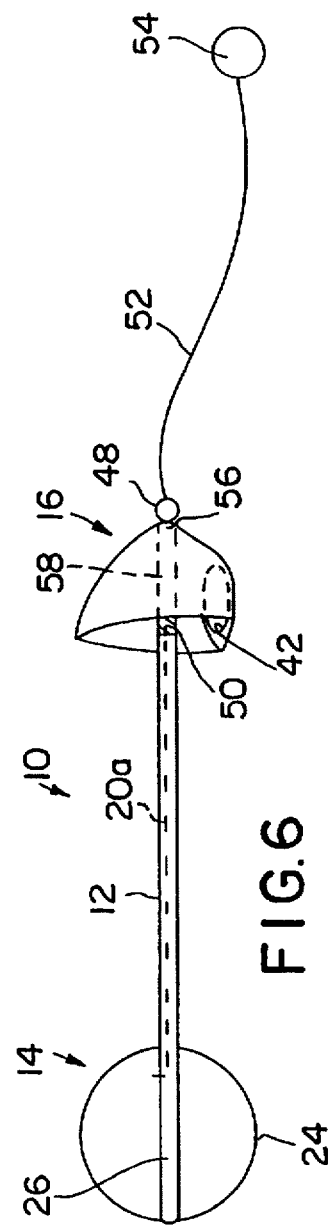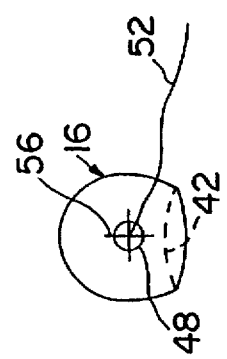

APPARATUS FOR TREATING INCONTINENCE IN FEMALES

CROSS REFERENCE TO PATENT OFFICE DISCLOSURE DOCUMENT

The application is related to United States Disclosure Document No. 393030 filed Feb. 14, 1996 with the United States Patent and Trademark Office pursuant to the disclosure document program.

BACKGROUND OF THE INVENTION

The invention relates to an apparatus and method for treating incontinence in females, especially for treating urinary incontinence.

Urinary incontinence is a common problem in women. This is, in large part, due to laxity of bladder support structures brought on by pregnancy and/or aging. The magnitude of this problem is evidenced by increasingly large expenditures each year on products such as incontinence diapers and other protective clothing. Surgical correction is possible in some cases, but is an invasive and costly procedure. Foley-type catheters are another solution, but require the wearing of a urine collection bag, and this type of catheter is associated with frequent infections. Urethral catheters with valves have been designed, but have not been widely used.

U.S. Pat. No. 5,090,424 to Simon et al. discloses a conformable urethral plug which has an inflatable element and which is removed each time the patient wishes to urinate, and then is reinserted. This device has the disadvantage of needing to be physically entirely removed and reinserted several times a day, leading to inconvenience, and the potential for irritation and/or infection.

It is clear that the need remains for an apparatus and method for treating urinary incontinence in women which does not require the use of collection bags, or repeated insertion and removal, and which does not lead to excessive irritation and/or infection.

It is therefore the primary object of the present invention to provide an apparatus for treating urinary incontinence in women which is indwelling and easy to operate.

It is a further object of the present invention to provide an apparatus which is easily inserted by a doctor or a patient.

It is a still further object of the present invention to provide an apparatus which is reliable and inexpensive, and simple in use.

It is a further object of the present invention to provide an apparatus the use of which does not lead to irritation and/or frequent infections.

It is a still further object of the present invention to provide a method for treating urinary incontinence in women using an apparatus according to the present invention.

Other objects and advantages will appear hereinbelow.

SUMMARY OF THE INVENTION

In accordance with the present invention, the foregoing objects and advantages are readily attained.

According to the invention, an apparatus is provided for treating incontinence in females, comprising: an elongate body member having a first end and a second end; an internal plug member positioned at the first end of the body member; an external retaining member positioned at the second end, at least one member of the internal plug member and the external retaining member being moveable longitudinally with respect to the other member of the internal plug member and the retaining member; and means for longitudinally securing the at least one member relative to the other member, whereby the elongate body member can be positioned in a urethra with the plug member positioned at an interior opening of the urethra and with the retaining member positioned at an exterior opening of the urethra.

In further accordance with the invention, the internal plug member is preferably an inflatable balloon for substantially blocking flow of urine into the urethra.

In accordance with a preferred embodiment, the apparatus of the present invention preferably further comprises means for selectively inflating and deflating the balloon between an inflated position wherein a flow of urine into the urethra is substantially blocked and a deflated position wherein flow into the urethra is substantially unblocked.

According to an alternative embodiment of the invention, the apparatus preferably further comprises a flexible member extending from the second end of the elongate body member, the retaining member being slidably positioned on the flexible member, and wherein the means for longitudinally securing comprises means for securing the retaining member relative to the body member.

In further accordance with the invention, a method is provided for treating incontinence in females which comprises the steps of providing an apparatus comprising an elongate body member having a first end and a second end; an internal plug member positioned at the first end of the body member; an external retaining member positioned at the second end, at least one member of the internal plug member and the external retaining member being movable longitudinally with respect to the other member of the internal plug member and the retaining member; and means for longitudinally securing the at least one member relative to the other member, wherein the internal plug member comprises an inflatable balloon in a deflated condition; positioning the elongate body member in the urethra with the internal plug member positioned at an interior opening of the urethra; moving the retaining member relative to the plug member so as to position the retaining member at the exterior opening of the urethra; securing the retaining member relative to the plug member at the exterior opening of the urethra; and selectively inflating and deflating the balloon between an inflated condition wherein the plug member substantially seals the interior opening of the urethra and the deflated condition wherein the plug member does not substantially seal the interior opening of the urethra.

BRIEF DESCRIPTION OF THE DRAWINGS

A detailed description of preferred embodiments of the present invention follows, with reference to the attached drawings wherein:

FIG. 1 is a side schematic view of an apparatus for treating incontinence in females in accordance with the present invention;

FIG. 2 is a side schematic view of the apparatus of FIG. 1, with a retaining member and balloon both in an expanded position;

FIG. 3 is an end view of the apparatus of FIG. 2 showing the expanded retaining structure of same;

FIG. 4 is an end view of a retaining structure of the embodiment of FIGS. 1–3;

FIG. 5 is a side schematic view of an alterative embodiment of the present invention;

FIG. 6 is a side schematic view of the alternative embodiment of FIG. 5 with the balloon in an inflated condition and the retaining member engaged on a knob structure; and FIG. 7 is an end view showing the retaining structure of the apparatus of FIG. 6.

DETAILED DESCRIPTION

In accordance with the invention, a method and apparatus are provided for treating incontinence, especially urinary incontinence, in females. In accordance with the invention, an apparatus is provided which is an indwelling apparatus having structure allowing the patient and/or attendant to the patient to selectively block and unblock the flow of urine from the bladder into the urethra for voiding as desired.

Referring now to the drawings, FIG. 1 shows an apparatus 10 having a substantially elongate body member 12, a plug structure 14, retaining structure 16 and a bulb structure 18 for selectively expanding plug structure 14 as will be thoroughly discussed below.

Body member 12 is preferably a substantially elongate tube structure which is preferably substantially rigid and resilient so as to adapt to angles which may be required during use. Body member 12 preferably defines two lumens or passages which are shown schematically by dashed lines 20, 22. Body member 12 preferably has a length of about 3 to about 6 inches, typically about 4 inches, and preferably has a relatively narrow diameter, sufficient to accommodate lumens 20, 22 and yet sufficiently small to allow flow through the urethra when body member 12 is positioned therein.

Plug member 14 preferably includes an inflatable balloon 24 positioned at a first or distal end 26 of body member 12. Balloon 24 is preferably inflated and deflated to an expanded position (FIG. 2) wherein balloon 24 is sufficiently large to seal an interior opening of a urethra, and a deflated position (as shown in FIG. 1) wherein balloon 24 is sufficiently small that apparatus 10 can be readily inserted through the urethra so as to position balloon 24 at the interior opening of the urethra, preferably at the vesico-urethral opening. Balloon 24 may be provided of any suitable material so as to provide desired expansion or inflation responsive to a reasonable influx of inflation fluid as will be further discussed below.

Plug member 14 preferably further includes an internal retaining structure 28 also positioned at distal end 26 of body member 12. As shown in FIG. 1–3, internal retaining structure 28 preferably includes a plurality of flexible struts 30 having first ends 32 connected to or extending from distal end 26 and having second ends 34 extending away from first ends 32 so that struts 30 are generally longitudinally aligned with elongate body member 12. In accordance with the invention, struts 30 are preferably flexible and biased toward a substantially straight position as shown in FIG. 1. Struts 30 arranged as shown in FIG. 1 form a compressible member which, upon compression, expands to a radially expanded position as shown in FIGS. 2 and 3. As will be discussed below, this is advantageous in that during use of apparatus 10, balloon 24 is deflated to allow flow from the bladder into the urethra. When balloon 24 is deflated, struts 30 in the radially expanded position shown in FIGS. 2 and 3 serve to hold apparatus 10 in position so that, when desired, balloon 24 can be re-inflated in the desired position so as to sealingly engage the interior opening of the urethra as desired.

Struts 30 may suitably be compressed to the radially expanded position through any means, but are preferably operated by elongate members such as ligatures 36 which are preferably slidably arranged in lumen 22, and are connected at one end to second or distal ends 34 of struts 30, and which extend through body member 12 and retaining structure 16 for use in securing structure 16 at a desired position relative to plug member 14 as will be thoroughly discussed below. In this way, ligatures 36 can be tensioned so as to assert compressive force on distal ends 34 of struts 30 and thereby cause an outward flexing of each strut 30 to the radially expanded position shown in FIGS. 2 and 3.

Retaining structure 16 is preferably a substantially hemispherical, dome or cone-shaped molded rubber or other flexible material structure which is slidably mounted on body member 12 so as to be longitudinally movable with respect to plug structure 14. Referring to FIG. 4, retaining structure 16 preferably has one centrally located aperture 38 for slidably receiving body member 12, and may also suitably have a pair of substantially centrally located apertures 40 for receiving ligatures 36. As shown in FIGS. 2 and 4, when retaining structure 16 is positioned as desired, ligatures 36 may suitably be tied on the proximal end of apertures 40 so as to secure retaining structure 16 in position against movement away from plug structure 14. Referring to FIGS. 1 and 2, retaining structure 16 also preferably includes an opening 42 arranged to be positioned downwardly away from body member 12. Opening 42 advantageously serves to direct flow from the urethra during use of apparatus 10 away from the longitudinal axis of body member 12 and, thereby, away from the hands of the user as desired.

Still referring to FIGS. 1 and 2, bulb structure 18 is preferably provided and communicates with balloon 24 through lumen 20 so as to provide inflation fluid as desired. Bulb structure 18 in accordance with the invention is preferably a flexible bulb structure containing liquid or air or some other suitable inflation fluid medium. Bulb structure 18 may suitably be connected to lumen 20 through tube 44 as shown. In further accordance with the invention, bulb structure 18 preferably also includes a check valve 46 for releasably preventing backflow from tube 44 into bulb 18. In this manner, bulb structure 18 can be compressed so as to drive inflation fluid through tube 44 and lumen 20 into balloon 24 for inflation of same. When it is desired to deflate balloon 24 and thereby allow flow from the bladder into the urethra, check valve 46 is manually actuated so as to allow inflation fluid to return into bulb 18, thereby deflating balloon 24 and allowing flow into the interior opening of the urethra.

It should be noted that although the present embodiment is described in terms of a bulb structure which is compressed to drive fluid into balloon 24, numerous other means for selectively inflating and deflating balloon 24 with inflation fluid could of course be provided.

Referring collectively to FIGS. 1–4, the method for implanting and operating apparatus 10 in accordance with the present invention will be described.

The apparatus is provided initially in the condition shown in FIG. 1, with retaining structure 16 loosely and slidably supported on body member 12, with balloon 24 in a deflated condition, and with struts 30 in a substantially straight or radially withdrawn position. In this condition, it is readily apparent that apparatus 10 has a narrow profile and can be readily inserted into the urethra of the patient to be treated as desired. Once the body member 12 is sufficiently inserted into the urethra that plug structure 14 extends beyond the interior opening of the urethra, fluid from bulb structure 18 is driven through tube 44 and lumen 20 into balloon 24 as desired so as to inflate balloon 24 to the inflated condition as shown in FIG. 2. Check valve 46 serves to releasably hold fluid within tube 44, lumen 20 and balloon 24 as desired. Next, by pulling on ligatures 36, inflated balloon 24 may be sealably engaged with the interior opening of the urethra, and retaining structure 16 can then be slidably positioned along body member 12 so as to snugly engage the exterior opening of the urethra as desired. At this position, slight additional tension on ligatures 36 results in the inward compression of struts 30, thereby flexing same to the radially expanded position as shown in FIGS. 2 and 3. Ligatures 36 are then preferably tied across apertures 40 as shown in FIG. 4 so as to releasably hold body member 12 with plug structure 14 positioned at the interior opening of the urethra, and with retaining structure 16 located at the exterior opening of the urethra. Also at this point, balloon 24 has sealably engaged the interior opening of the urethra and thereby substantially prevents flow from the bladder into the urethra as desired.

When it is desired to allow flow through the urethra and thereby void the bladder, the patient or attending personnel can manually release check valve 46 so as to allow fluid to flow from balloon 24 through lumen 20 and tube 44 back into bulb structure 18. This deflates balloon 24 to the deflated condition in FIG. 1, and thereby allows flow from the bladder into the urethra, into retaining structure 16 and through opening 42 as desired. During this process, radially expanded struts 30 serve to prevent apparatus 10 from being ejected from the urethra while balloon 24 is deflated. When sufficient fluid has been removed from the bladder, bulb structure 18 can then suitably be used to again drive inflation fluid back through tube 44 and lumen 20 into balloon 24 so as to inflate balloon 24 into the inflated condition as shown in FIG. 2, thereby once again substantially sealing the interior opening of the urethra as desired.

It should be readily appreciated that apparatus 10 according to the invention provides an indwelling apparatus which can be operated as desired by the patient or attending personnel, and which clearly does not require frequent insertion and removal. Further, this apparatus is simple and efficient in structure and easy to operate.

Referring now to FIGS. 5–7, an alternative embodiment of the present invention will be described, and like reference numerals will be used to indicate similar elements. Referring to FIG. 5, elongate body member 12 of this embodiment is preferably provided having a single lumen 20a communicating with balloon 24 of plug structure 14 so as to allow inflation and deflation of same. Body member 12 is preferably also provided with a knob structure 48 at proximal or second end 50 of body member 12. A nylon string or other suitable ligature 52 is preferably attached to and extends from proximal end 50 of body member 12 as shown, and retaining structure 16 is slidably positioned along nylon string 52. A retaining knob or bead 54 is preferably provided at a position along nylon string 52 so as to limit the maximum movement of retaining structure 16 away from balloon 24 in accordance with the invention.

Body member 12 preferably further includes a portion 58 communicated with lumen 20a which is made from a self-sealing material for use in connection with an inflation needle to charge balloon 24 with an inflation fluid, and automatically seal upon removal of the inflation needled as desired. Self-sealing portion 58 may suitably be made of self-sealing rubber or like material which seals or substantially seals after a puncturing member is removed.

In operation, the embodiment of FIGS. 5–7 is positioned within the urethra as desired, balloon 24 is inflated, and retaining structure 16 is engaged with knob 48 so as to hold same in place with inflated balloon 24 sealingly engaging the interior opening of the urethra. FIG. 6 shows apparatus 10 in accordance with this embodiment of the invention with balloon 24 in an inflated condition and with retaining structure 16 engaging knob 48.

Referring to FIG. 7, an end view of retaining structure 16 according to this embodiment is shown, wherein structure 56 is provided for releasably engaging knob 48 as desired. As shown in FIGS. 5–7, retaining structure in accordance with this embodiment also has opening 42 for directing flow as desired in accordance with the invention.

In further accordance with this embodiment of the invention, knob 48 is preferably longitudinally adjustable or positionable with respect to plug structure 14 so as to accommodate various positions which may be required for engaging retaining structure 16. In this manner, advantageously, apparatus 10 can readily be adjusted to various lengths or distances between plug structure 14 and retaining structure 16 as may be required by various patients. Knob 48 may suitably be adjustable relative to plug structure 14 through any longitudinally adjustable connection or mounting of knob 48 relative to body member 12 and/or nylon string 52. For example, releasable stop means (not shown) could be provided for releasably secured knob 48 along nylon string 52. Alternatively, knob 48 could be structurally movable with respect to body member 12, for example through a threaded engagement. Of course, numerous other means may be provided for accomplishing the desired releasable positioning of knob 48 in accordance with the invention.

Retaining structure 16 in accordance with this embodiment is preferably sufficiently flexible that engaging structure 56 such as a cruciate slit as shown in the drawings can be securely engaged and released from knob 48 as desired.

Referring collectively to FIGS. 5–7, apparatus 10 in accordance with this embodiment is installed and used as follows. For installation, apparatus 10 is provided in the condition illustrated in FIG. 5, with balloon 24 deflated and retaining structure 16 disengaged from knob structure 48. Body member 12 is preferably positioned within the urethra, with balloon structure 24 extending to and preferably slightly beyond the interior opening of the urethra. Inflation fluid is then driven from a source (not shown in FIGS. 5–7) through lumen 20a so as to inflate balloon 24 to the inflated condition as shown in FIG. 6. Body member 12 is then positioned so as to snugly engage balloon 24 with the interior opening of the urethra, and knob 48 is then preferably longitudinally adjusted with respect to body member 12 and balloon 24 for proper positioning so as to engage retaining structure 16. Once knob 48 is properly located, retaining structure 16 is then positioned along nylon string 52 toward balloon 24 so as to engage knob 48 with engaging structure 56. In this position, body member 12 is securely held within the urethra with balloon 24 sealingly engaging the interior opening of the urethra and retaining structure 16 snugly positioned with respect to the exterior opening of the urethra. When it is desired to void fluids from the bladder, retaining structure 16 is disengaged from knob 48, allowing body member 12 to migrate slightly inwardly, thereby removing inflated balloon 24 from sealing engagement with the interior opening of the urethra and allowing flow into the urethra to retaining structure 16 and out of opening 42 as desired. When sufficient fluids have been removed from the bladder, nylon string 52 can be pulled gently proximally, while retaining structure 16 is pressed gently distally so as to re-engage engaging structure 56 with knob structure 48, thereby again sealingly positioning inflated balloon 24 with respect to the interior opening of the urethra.

In accordance with this embodiment, it should be appreciated that balloon 24 is inflated upon installation of apparatus 10, and remains inflated until apparatus 10 needs to be removed. Thus, advantageously, no inflating and deflating structure is required to be permanently associated with apparatus 10 in accordance with the use and operation of same.

In accordance with this embodiment of the invention, it should be readily apparent that an apparatus 10 has been provided for relatively long-term or permanent installation and treatment of incontinence in females, which apparatus avoids the need for several daily insertions and removals, and which allows for a convenient and relatively simple procedure for removing fluids from the bladder.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An apparatus for treating incontinence in females, comprising:
   an elongate body member having an outside diameter, a first end and a second end;
   an internal plug member positioned at the first end of the body member;
   an external retaining member positioned at the second end and having a flow passage, at least one member of the internal plug member and the external retaining member being moveable longitudinally with respect to the other member of the internal plug member and the retaining member; and
   means for longitudinally securing the at least one member relative to the other member, whereby the elongate body member can be positioned in a urethra with the plug member positioned at an interior opening of the urethra and with the retaining member positioned at an exterior opening of the urethra, and wherein the internal plug member is operable to selectively provide urine flow in the urethra exterior of the outside diameter of the elongate body member and through the flow passage of the external retaining member.

2. An apparatus according to claim 1, further comprising interior retaining means positioned at the first end for retaining the elongate body member within the urethra.

3. An apparatus according to claim 1, wherein the retaining means comprises a substantially hemispheric member slidably positioned on the elongate body member and having means for directing flow at an angle with respect to a longitudinal axis of the elongate body member.

4. An apparatus according to claim 1, further comprising a flexible member extending from the second end, the retaining member being slidably positioned on the flexible member, and wherein the means for longitudinally securing comprises means for securing the retaining member relative to the body member.

5. An apparatus according to claim 1, wherein the internal plug member comprises an inflatable balloon for substantially blocking flow of urine into the urethra.

6. An apparatus according to claim 5, further comprising means for selectively inflating and deflating the balloon between an inflated position wherein flow of urine into the urethra is substantially blocked and a deflated position wherein flow of urine into the urethra is substantially unblocked.

7. An apparatus according to claim 6, further comprising interior retaining means positioned at the first end for retaining the elongate body member within the urethra when the balloon is deflated.

8. An apparatus according to claim 5, further comprising means for inflating the balloon with the elongate body member positioned in the urethra.

9. An apparatus according to claim 8, wherein the source of inflation fluid comprises a bulb communicated with the fluid passage and containing inflation fluid whereby compression of the bulb drives the inflation fluid through the fluid passage into the balloon to inflate the balloon.

10. An apparatus according to claim 9, further comprising a valve member associated with the bulb for releasably blocking flow of inflation fluid into the bulb whereby the balloon is selectively inflatable for blocking flow of urine into the urethra.

11. An apparatus according to claim 8, wherein the means for inflating comprises a fluid passage associated with the elongate body member and communicated at one end with the balloon and communicated at the other end with a source of inflation fluid for inflating the balloon.

12. An apparatus according to claim 11, wherein the fluid passage comprises a lumen running lengthwise along the elongate body member.

13. An apparatus according to claim 12, wherein the lumen is defined within the elongate body member.

14. An apparatus for treating incontinence in females; comprising:
   an elongate body member having a first end and a second end;
   an internal plug member positioned at the first end of the body member;
   an external retaining member positioned at the second end, at least one member of the internal plug member and the external retaining member being moveable longitudinally with respect to the other member of the internal plug member and the retaining member;
   means for longitudinally securing the at least one member relative to the other member, whereby the elongate body member can be positioned in a urethra with the plug member positioned at an interior opening of the urethra and with the retaining member positioned at an exterior opening of the urethra, wherein the internal plug member comprises an inflatable balloon for substantially blocking flow of urine into the urethra;
   means for selectively inflating and deflating the balloon between an inflated position wherein flow of urine into the urethra is substantially blocked and a deflated position wherein flow of urine into the urethra is substantially unblocked; and
   interior retaining means positioned at the first end for retaining the elongate body member within the urethra when the balloon is deflated.

15. An apparatus according to claim 14, wherein the interior retaining means comprises expandable means expandable to a radially expanded position for holding the elongate body member within the urethra.

16. An apparatus according to claim 15, further comprising means for expanding the expandable means with the elongate body member positioned in the urethra.

17. An apparatus according to claim 16, wherein the elongate body member defines a first lumen and a second lumen, wherein the first lumen accommodates the means for selectively inflating and deflating and the second lumen accommodates the means for expanding.

18. An apparatus according to claim 16, wherein the elongate body member defines a lumen and wherein the means for expanding is accommodated in the lumen.

19. An apparatus according to claim 16, wherein the means for expanding comprises means extending through the elongate body member and secured to the expandable means at one end, and passing through the retaining member at the other end, for exerting a longitudinally compressive force on the expandable means so as to expand the expandable means to the radially expanded position.

20. An apparatus according to claim 19, wherein the expandable means comprises a plurality of flexible struts having first ends and second ends, wherein the first ends are fixed relative to the elongate body member and the second ends extend longitudinally away from the first ends and the elongate body member, wherein the flexible struts are biased toward a substantially straight radially withdrawn position, and wherein the means for expanding is secured to the second ends for exerting the longitudinally compressive force on the second ends to flex the struts and expand the expandable means to the radially expanded position.

21. An apparatus for treating incontinence in females, comprising:
an elongate body member having a first end and a second end;
an internal plug member positioned at the first end of the body member;
an external retaining member positioned at the second end, at least one member of the internal plug member and the external retaining member being moveable longitudinally with respect to the other member of the internal plug member and the retaining member;
means for longitudinally securing the at least one member relative to the other member, whereby the elongate body member can be positioned in a urethra with the plug member positioned at an interior opening of the urethra and with the retaining member positioned at an exterior opening of the urethra; and
interior retaining means positioned at the first end for retaining the elongate body member within the urethra.

22. An apparatus according to claim 21, wherein the interior retaining means comprises expandable means expandable to a radially expanded position for holding the elongate body member within the urethra.

23. An apparatus according to claim 22, further comprising means for expanding the expandable means with the elongate body member within the urethra.

24. An apparatus according to claim 23, wherein the means for expanding comprises means extending through the elongate body member and secured to the expandable means at one end, and passing through the retaining member at the other end, for exerting a longitudinally compressive force on the expandable means so as to expand the expandable means to the radially expanded position.

25. An apparatus according to claim 24, wherein the expandable means comprises a plurality of flexible struts having first ends and second ends, wherein the first ends are fixed relative to the elongate body member and the second ends extend longitudinally away from the first ends and the elongate body member, wherein the flexible struts are biased toward a substantially straight radially withdrawn position, and wherein the means for expanding is secured to the second ends for exerting the longitudinally compressive force on the second ends to flex the struts and expand the expandable means to the radially expanded position.

26. An apparatus according to claim 25, wherein the elongate body member defines a lumen and wherein the means for expanding is accommodated in the lumen.

27. An apparatus for treating incontinence in females, comprising:
an elongate body member having a first end and a second end;
an internal plug member positioned at the first end of the body member;
an external retaining member positioned at the second end, at least one member of the internal plug member and the external retaining member being moveable longitudinally with respect to the other member of the internal plug member and the retaining member;
means for longitudinally securing the at least one member relative to the other member, whereby the elongate body member can be positioned in a urethra with the plug member positioned at an interior opening of the urethra and with the retaining member positioned at an exterior opening of the urethra, and
wherein the retaining means comprises a substantially hemispheric member slidably positioned on the elongate body member and having means for directing flow at an angle with respect to a longitudinal axis of the elongate body member.

28. An apparatus according to claim 27, wherein the means for directing flow comprises an opening positioned in a side wall of the substantially hemispheric member.

29. An apparatus according to claim 27, wherein the means for longitudinally securing comprises at least one flexible member fixed relative to the plug member and securably passing through the hemispheric member, whereby securing the flexible member to the hemispheric member fixes the hemispheric member against longitudinal movement away from the plug member.

30. An apparatus for treating incontinence in females, comprising:
an elongate body member having a first end and a second end;
an internal plug member positioned at the first end of the body member;
an external retaining member positioned at the second end, at least one member of the internal plug member and the external retaining member being moveable longitudinally with respect to the other member of the internal plug member and the retaining member;
means for longitudinally securing the at least one member relative to the other member, whereby the elongate body member can be positioned in a urethra with the plug member positioned at an interior opening of the urethra and with the retaining member positioned at an exterior opening of the urethra; and
a flexible member extending from the second end, the retaining member being slidably positioned on the flexible member, and wherein the means for longitudinally securing comprises means for securing the retaining member relative to the body member.

31. An apparatus according to claim 30, further comprising stop means positioned on the flexible member for limiting a maximum movement of the retaining member away from the plug member along the flexible member.

32. An apparatus according to claim 30, wherein the elongate body member is a rod and the flexible member is a string.

33. An apparatus according to claim 30, wherein the retaining member comprises a substantially dome shaped member having the flexible member passing therethrough, and having an opening in a side wall of the dome shaped member for directing flow out of the dome shaped member.

34. An apparatus according to claim 30, wherein the internal plug member comprises an inflatable balloon.

35. An apparatus according to claim 34, further comprising means for inflating the balloon with the elongate body member positioned in the urethra.

36. An apparatus according to claim 30, wherein the means for securing comprises knob means positioned at the second end of the elongate body member, and wherein the retaining member has knob engaging means for releasably engaging the knob means in a blocking position wherein the plug member is substantially sealingly positioned in the interior opening of the urethra.

37. An apparatus according to claim 36, wherein the knob means is longitudinally positionable relative to the elongate body member whereby a distance between the plug member and the retaining member in the blocking position can be adjusted.

38. A method for treating incontinence in females, comprising the step of:

providing an apparatus comprising an elongate body member having an outside diameter, a first end and a second end; an internal plug member positioned at the first end of the body member; an external retaining member positioned at the second end and having a flow passage, at least one member of the internal plug member and the external retaining member being movable longitudinally with respect to the other member of the internal plug member and the retaining member; and means for longitudinally securing the at least one member relative to the other member, wherein the internal plug member comprises an inflatable balloon in a deflated condition;

positioning the elongate body member in the urethra with the internal plug member positioned at an interior opening of the urethra;

moving the retaining member relative to the plug member so as to position the retaining member at the exterior opening of the urethra;

securing the retaining member relative to the plug member at the exterior opening of the urethra; and selectively inflating and deflating the balloon between an inflated condition wherein the plug member substantially seals the interior opening of the urethra and the deflated condition wherein the plug member does not substantially seal the interior opening of the urethra and urine flow is allowed in the urethra exterior of the outside diameter of the elongate body member and through the flow passage of the external retaining member.

39. A method for treating continence in females, comprising the steps of:

providing an apparatus comprising an elongate body member having a first end and a second end; an internal plug member positioned at the first end of the body member; an external retaining member positioned at the second end, at least one member of the internal plug member and the external retaining member being movable longitudinally with respect to the other member of the internal plug member and the retaining member; and means for longitudinally securing the at least one member relative to the other member, wherein the internal plug member comprises an inflatable balloon in a deflated condition and wherein the apparatus further includes knob a means associated with the second end of the elongate body member, and the retaining member further comprises knob engaging for releasably engaging the knob means;

positioning the elongate body member in the urethra with the internal plug member positioned at an interior opening of the urethra;

inflating the balloon; and selectively moving the retaining member relative to the plug member between a sealing position wherein the balloon is sealingly positioned at the interior opening of the urethra and the knob engaging means is engaged with the knob and a voiding position wherein the knob engaging means is disengaged from the knob and wherein the balloon is at least partially spaced from the interior opening of the urethra.

\* \* \* \* \*

UNITED STATES PATENT AND TRADEMARK OFFICE
CERTIFICATE OF CORRECTION

PATENT NO. : 5,792,042
DATED : AUGUST 11, 1998
INVENTOR(S) : KENNETH L. COHEN ET AL.

It is certified that error appears in the above-identified patent and that said Letters Patent is hereby corrected as shown below:

Column 12, line 12, claim 39, delete "continence" and insert --incontinence--.

Column 12, line 26, claim 39, after "includes" insert --a-- and after "knob" delete "a means".

Column 12, line 29, after "knob" delete "means".

Column 12, line 28, after "engaging" insert --means--.

Signed and Sealed this

Tenth Day of November 1998

Attest:

BRUCE LEHMAN

*Attesting Officer*  *Commissioner of Patents and Trademarks*